Figure 1:
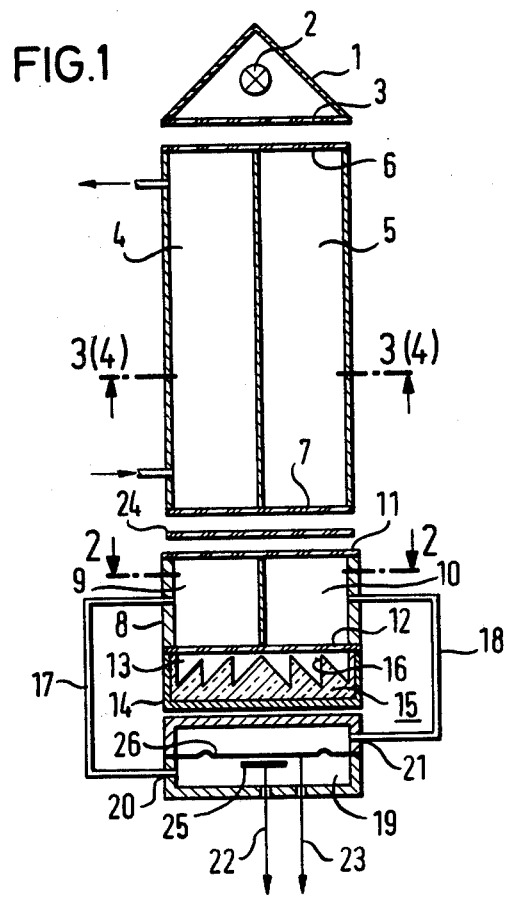

United States Patent [19]

Blunck

[11] 4,184,074
[45] Jan. 15, 1980

[54] NONDISPERSIVE INFRARED GAS ANALYSIS DEVICE

[76] Inventor: Otto H. Blunck, Trelleborgallee 2, Lubeck-Travemunde, Fed. Rep. of Germany

[21] Appl. No.: 922,315

[22] Filed: Jul. 6, 1978

[30] Foreign Application Priority Data

Nov. 15, 1977 [DE] Fed. Rep. of Germany ....... 2751047

[51] Int. Cl.² .......................................... G01N 21/26
[52] U.S. Cl. .................................................. 250/345
[58] Field of Search ................ 250/343, 344, 345, 373

[56] References Cited

U.S. PATENT DOCUMENTS

| | | | |
|---|---|---|---|
| 2,844,729 | 7/1958 | Winterling et al. | 250/345 |
| 3,725,702 | 4/1973 | Schaefer | 250/345 X |

Primary Examiner—Davis L. Willis
Attorney, Agent, or Firm—Roylance, Abrams, Berdo & Farley

[57] ABSTRACT

A body has two bores defining two cuvette chambers, one for holding a comparison gas and the other for holding a gas to be analyzed by comparison with the first. An infrared (IR) source at one end of the body provides in-phase radiation into the two cuvettes. At the other end is a window, a selective filter, a reception chamber for each cuvette, and an absorption chamber. The reception chambers are coupled to a device for producing a signal representing the difference in radiation reaching the reception chambers. The reception and absorption chambers are separated by a low reflectance window and the absorption chamber contains an IR absorbing body of glass, polymethacrylate or the like with concentric grooves.

6 Claims, 4 Drawing Figures

U.S. Patent

Jan. 15, 1980

4,184,074

NONDISPERSIVE INFRARED GAS ANALYSIS DEVICE

This invention relates to an infrared gas analysis device in which infrared energy is caused to pass through a gas to be analyzed and a comparison gas to a detection device, and in which reflection of energy back into the gases is substantially prevented.

BACKGROUND OF THE INVENTION

The prior art devices in this general field include those in which infrared radiation is caused to pass through separate paths, through a comparison gas and a gas to be analyzed so that the relative absorption characteristics of the two gases can be determined. In German Pat. No. 730,478, a device of this general type is shown in which in each ray path equal receiving layers are disposed among themselves and the differences of the radiation energy absorbed in the receiving layers is measured as a measure of the concentration of the gas component which is being determined. In the case of this device, it is a disadvantage that the rear walls of the receiving layers are made of a material which is impermeable to radiation so that the radiation is reflected from those rear walls and proportionately once more passes through the receiving layers and the cuvettes and a non inconsiderable portion of this radiation again reaches the radiator unit. From there, a part of the radiation is again reflected back through the cuvettes into the measuring chamber. As a consequence, ever larger portions of the marginal zones of the absorption areas are stimulated and corresponding transverse responses for interfering gases develop. The path from the radiator unit to the receiving layers and back may then be traversed several times, depending upon the absorption conditions in the intermediate gas layers and windows. All changes in the absorption and deflection behavior in the construction components of this device, for example, surface influences as a result of changes in temperature, precipitations of moisture, chemical reactions, etc., are therefore contributing factors to instabilities of the zero point of the device and of the sensitivity thereof.

Another device is shown in German Pat. No. 976,290, wherein the rear wall of the receiving layers consists of a raw material permeable to the radiation. This is an effort to reduce the reflection, but does not, by itself, eliminate the above-described deficiencies because, on the one hand, radiation emanating from the source of radiation is reflected again as a result of the rear window with the above-described consequences. On the other hand, radiation from the surroundings may penetrate, for example, from outside sources of heat, which emit radiation having portions in the spectral range of interest. As a result of changes in the environment, the residual radiation entering through the rear window into the receiving layers is undefined and not constant, as a result of which insufficient stability of the device results.

In the case of many measures which have been attempted for improvement in nondispersive infrared gas analysis devices, the achievement of a stable zero point has been regarded as a preeminent requirement. Zero point stability was sought by the arrangement of several receiving chambers acted upon by the radiation, by special forming or shaping of the receiving chambers, etc., and the measures taken in these devices led to the construction of more complicated apparatus which is more subject to breakdowns. On the other hand, mechanisms have been known to aid in the establishment and control of the zero point, including automatic regulation at certain time intervals, either fixed or adjustable, so that the improving measures previously mentioned for the IR analysis devices themselves are no longer decisive for the achievement of a stable zero point.

BRIEF DESCRIPTION OF THE INVENTION

An object of the present invention is to create a nondispersive IR gas analysis device which greatly improves the stability of measurements made therein.

Briefly described, the apparatus of the invention includes a nondispersive infrared gas analysis device including first and second gas-containing cuvettes adapted, respectively, to contain a gas to be analyzed and a comparison gas, said cuvettes having radiation transparent means at both ends thereof; a source of radiation coupled to the transparent means at one end of the cuvettes to pass isophase radiation thereto; a detector unit at the other end of said cuvettes to receive radiation emanating from said cuvettes for producing a differential signal representative of differences in radiation emanating from said cuvettes, said detector unit comprising a body; means defining first and second reception chambers in said body adapted to receive radiation from said first and second cuvettes, respectively; filter means between said cuvettes and said chambers for selectively passing into said chambers radiation at a predetermined wavelength; an input window covering an end of said chambers adjacent said filter means; a second window covering the other end of said chambers, said second window being formed to be substantially free of reflection; means defining an infrared absorption chamber hermetically sealed from said reception chambers by said second window for absorbing infrared energy passing through said reception chambers; and means coupled to said reception chambers for producing the differential signals.

As previously indicated, the advantages achieved using the apparatus of this invention reside in the good measuring stability of the device. The infrared gas analyzer according to the invention contains substantially only circular components or bores and may therefore be produced at a reasonable cost. As a result of the compact construction, relatively small dimensions may be achieved. The device is sturdy and the individual construction parts are easily producible. As a result of the compact and symmetrical construction, the sensitivity to shocks and the effects of temperature are minimal.

Figure 2:
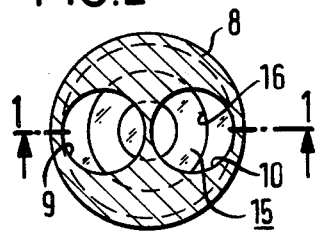
Figure 3:
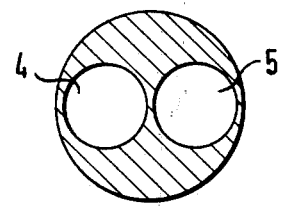
Figure 4:
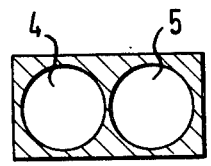

In order that the manner in which the foregoing and other objects are attained in accordance with the invention can be understood in detail, a particularly advantageous embodiment thereof will be described with reference to the accompanying drawings, which form a part of this specification and wherein:

FIG. 1 schematically shows a longitudinal section through a gas analyzer in accordance with the invention;

FIG. 2 shows a transverse section through the receiving arrangement of the apparatus of FIG. 1; and FIG. 3 and 4 show two different transverse sections through the divided cuvette.

As shown in FIG. 1, the analyzing device includes a source of infrared energy which will be described as a radiator unit consisting of a housing 1 and a window 3, the housing containing a thermal radiator 2. The radiation of radiator 2 can be modulated, by known devices which have not been illustrated, in such a way that radiation at the same phase is caused pass through the cuvette 4 which contains a gas to be analyzed and a cuvette 5 which contains the reference or comparison gas. The modulating means can include, for example, an electric pulse arrangement which delivers a rectangular wave voltage for the periodic heating of radiator 2. The radiation may additionally or alternatively be modulated by customary mechanical chopper or vibrator arrangement.

After passage through the divided cuvette having chambers 4 and 5, the radiation encounters a radiation filter 24 which allows passage of only radiation in the spectral range of interest. As a result of that, the cross response of the device for interfering gases is reduced. It is therefore not necessary to always arrange two successive receiving chambers in the path of the rays as a result of which weak absorptions are to be compensated by interfering gases. The rays then pass into a receiving arrangement which contains two chambers 9 and 10 which are formed as circular bores in a cylindrical block 8, as shown in FIG. 2. The chambers are sealed at the front or input side of the rays by means of a window 11 and on the rear side with a window 12. At least the window 12 is developed free of reflections, each of the windows 11 and 12 covering up the entire end of block 8. The chambers 9 and 10 are arranged and dimensioned such that they always have a square cross section in planes containing their axes of symmetry. Stated differently, they are dimensioned so that the length of each chamber equals the diameter of the chamber. As a result of this, the formation and conversion of pressure impulses created by the absorption of the radiation in the chambers is favored. Because of the development of chambers 9 and 10, as described, a compact closely adjoining arrangement of the measuring chambers is achieved. Thus, even slight temperature differences in the measuring chamber arrangement, due to extraneous effects, can be avoided. Such temperature differences could influence the absorption behavior in the chamber through the effect of spreading of shocks.

The use of continuous windows 11 and 12, rather than two windows at each end adjacent the individual chambers, has the advantage that, as a result, an absolute symmetry of the arrangement is possible. In an equivalent development using two windows, the achievement of absolute symmetry causes difficulties because of the necessity for exceedingly precise arrangement thereof and the single window unit is therefore preferred.

In the path of the rays on the outlet ends of chamber 9 and 10, through window 12, there is provided a chamber 13 into which there is inserted a body 15 which is made of an IR absorbing dielectric material such as glass or a glass-like transparent plastic made of polymethacrylates. Body 15 is formed as a round disc provided with a plurality of concentric grooves in the major face which faces toward the cuvettes, the grooves being formed so that, when viewed in section as shown in FIG. 1, the grooves have a sawtooth-like profile. As will be observed, at least one edge or surface 16 of the sawtooth extends parallel to the direction of radiation.

In the chamber 13, the entire radiation passing through window 12 from receiving chambers 9 and 10 is absorbed so that no portion of the radiation is reflected back into the receiving chambers. This is further favored by the geometric form of the body 15 since the radiation which penetrated from above into chamber 13 must be reflected at least a total of three times on the body 15 before it can again pass into chamber 9 and 10. Thus, the probability of absorption in the chamber 13 is great and the portion of the radiation returning toward the cuvettes is practically zero. The chambers 9 and 10 are therefore actually irradiated exclusively in a single direction.

Also, the chamber 13 is constructed so that the body disposed in it and made of IR absorbing dielectric material consists of a body fitted against the inside surface of the casing forming chamber 13 and by a centrally disposed conical shape in body 15. In this case, also, the radiation must be reflected at least three times before it can again enter into chambers 9 and 10. Radiation which possible is reflected back is so reduced in intensity that it is practically without significance because of the repeated opportunities for absorption by body 15. While this construction of chamber 13 is functionally very effective, this structure has the advantage of a relatively low constructional height and is thus preferred for reasons of compactness.

While the individual structural measures described, including the arrangement of the radiation filter 24, the use of a window 12 which is free of reflections, and the absorption of the radiation in chamber 13 which has penetrated chambers 9 and 10, will bring about improvements of the measuring characteristics if used individually, the decisive advantages with respect to stability and minimal cross response will result most advantageously by a combination of all three measures mentioned.

The chamber 9 is connected by a conduit 17 to one side of a membrane capacitor 19 unit at 20, and chamber 10 is connected with the other side of the membrane capacitor unit through a conduit 18, connected at 21. As will be recognized, changes in the absorption within chambers 9 and 10 will cause fluctuation in the position of the electrically conductive transverse membrane 26 through chamber 19, thereby varying the spacing between that membrane and a fixed electrode 25. This change of spacing alters the capacity between the membrane and the electrode, producing an electrical effect which can be measured by circuitry connected to conductors 22 and 23 which are attached to the fixed electrode and the membrane, respectively. The changes of capacity of the membrane capacitor 19 are processed into suitable measuring signals by means of a customary circuit which is connected to the conductors.

While the embodiment described herein has been shown with a membrane capacitor as a means for the formation of the differential signal from the individual signals produced as a result of the radiation absorption in the receiving chambers, it will be recognized that the invention can be used in conjuncture with other such means as, for example, thermoelectric sensors associated with chambers 9 and 10.

While one certain advantageous embodiment has been chosen to illustrate the invention, it will be understood by those skilled in the art that various changes and modifications can be made therein without departing from the scope of the invention as defined in the appended claims.

In respect to said nonreflective character of at least window 12 it should be noted that this character may be accomplished simply by abrading the surface or by electing a special kind of glas having a reflectance coefficient as low as possible.

What is claimed is:

1. A nondispersive infrared gas analysis device comprising
   first and second gas-containing cuvettes adapted, respectively, to contain a gas to be analyzed and a comparison gas, said cuvettes having radiation transparent means at both ends thereof;
   a source of radiation coupled to said transparent means at one end of the cuvettes to pass isophase radiation thereto;
   a detector unit at the other end of said cuvettes to receive radiation emanating from said cuvettes for producing a differential signal representative of differences in radiation emanating from said cuvettes, said detector unit comprising:
   a body;
   means defining first and second reception chambers in said body adapted to receive radiation from said first and second cuvettes, respectively;
   filter means between said cuvettes and said chambers for selectively passing into said chambers radiation at a predetermined wavelength;
   an input window covering an end of said chambers adjacent said filter means;
   a second window covering the other end of said chambers, said second window being formed to be substantially free of reflection;
   means defining an infrared absorption chamber hermetically sealed from said reception chambers by said second window for absorbing infrared energy passing through said reception chambers; and
   means coupled to said reception chambers for producing the differential signals.

2. A device according to claim 1 wherein each of said reception chambers has an axis of symmetry in the direction of travel of the radiation, and wherein each of said reception chambers has a square cross section in planes containing the axis of symmetry.

3. A device according to claim 1 wherein said means defining an absorption chamber includes a metallic body having a recess to define said chamber, and an infrared absorbing body in said recess, said body being formed as a disc having a plurality of concentric grooves in one face thereof, said grooves being formed to define a sawtooth pattern in transverse selection with at least one edge of the sawtooth extending parallel with the direction of radiation.

4. A device according to claim 3 wherein said infrared absorbing body is glass.

5. A device according to claim 3 wherein said infrared absorbing body is polymethacrylate.

6. A device according to claim 1 wherein said means defining an absorption chamber includes a metallic casing having a recess to define said chamber, and an infrared absorbing body in said recess, said absorbing body being made from glass or transparent polymethacrylate.

* * * * *